United States Patent [19]

Sicurelli, Jr. et al.

[11] Patent Number: 5,518,399
[45] Date of Patent: May 21, 1996

[54] METHOD OF RESTORING AN ENDODONTICALLY-TREATED TOOTH

[75] Inventors: Robert J. Sicurelli, Jr., Muttontown; Samuel Masyr, Brooklyn, both of N.Y.

[73] Assignee: Tru-Flex Post Systems, Inc., Muttontown, N.Y.

[21] Appl. No.: 126,631

[22] Filed: Sep. 27, 1993

[51] Int. Cl.$^6$ .................................................. A61C 5/08
[52] U.S. Cl. .................................................. 433/220
[58] Field of Search ......................... 433/175, 220, 433/221, 225

[56] References Cited

U.S. PATENT DOCUMENTS

| | | | |
|---|---|---|---|
| 622,670 | 4/1899 | Dwight | 433/221 |
| 732,922 | 7/1903 | Clark | 433/221 |
| 822,582 | 6/1906 | Carmichael | 433/220 |
| 1,218,289 | 3/1917 | Maker | 433/220 |
| 3,949,476 | 4/1976 | Kahn | 32/12 |
| 4,778,388 | 10/1988 | Yuda | 433/221 |
| 4,778,389 | 10/1988 | Salvo | 433/221 |
| 4,934,936 | 6/1990 | Miller | 433/221 |
| 4,936,776 | 6/1990 | Kwiatkowski | 433/220 |
| 4,952,150 | 8/1990 | Schiwiora et al. | 433/220 |
| 5,073,112 | 12/1991 | Weil | 433/221 |
| 5,074,792 | 12/1991 | Bernadat | 433/220 |

FOREIGN PATENT DOCUMENTS

| | | |
|---|---|---|
| 1541209 | 7/1969 | Germany . |
| 3643219 | 6/1988 | Germany . |
| WO91/071 | 5/1991 | WIPO . |

OTHER PUBLICATIONS

"A Comparison of Intracanal Stresses in a Post–Restored Tooth Utilizing the Finite Element Method", Cailleteau, Johnny G., Rieger, Monty R. and Akin, J. Ed, Journal of Endodontics, vol. 18, No. 11, Nov. 1992, pp. 540–544.
Flexi–Post & Flexi–Flange, Essential Dental Systems '89 Leuning Street, S. Hackensack, N.J. 07606, Advertisement, Dec. 1994.

*Primary Examiner*—Cary E. O'Connor
*Attorney, Agent, or Firm*—Stephen E. Feldman

[57] ABSTRACT

A method of installing a dental post and core system having a flexible post.

7 Claims, 2 Drawing Sheets

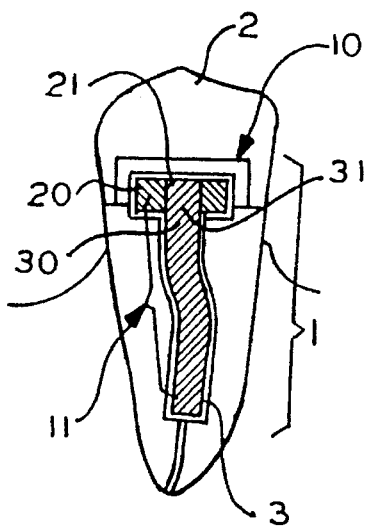
FIG. 1
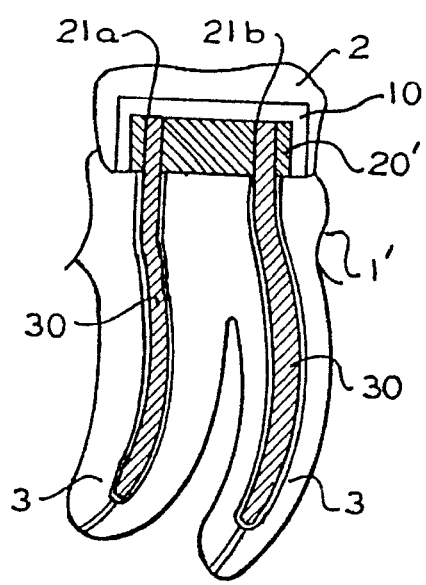
FIG. 2
FIG. 3
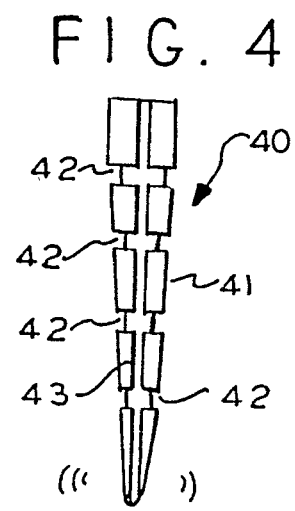
FIG. 4
FIG. 5
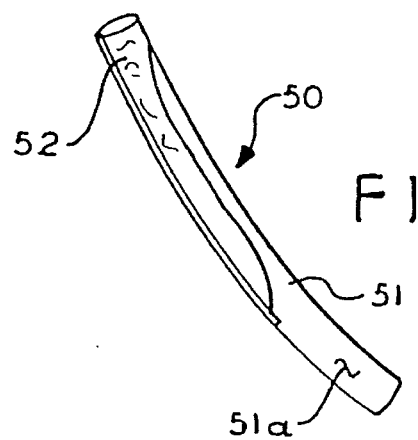

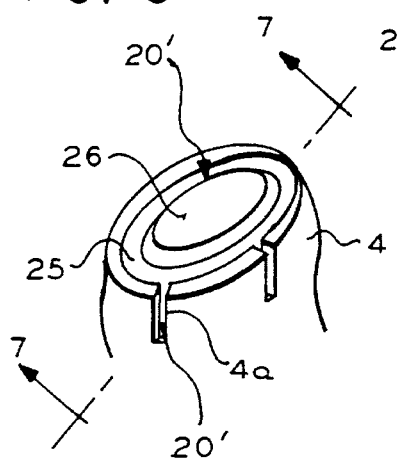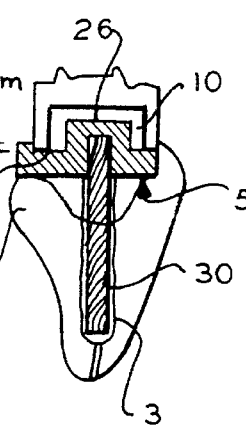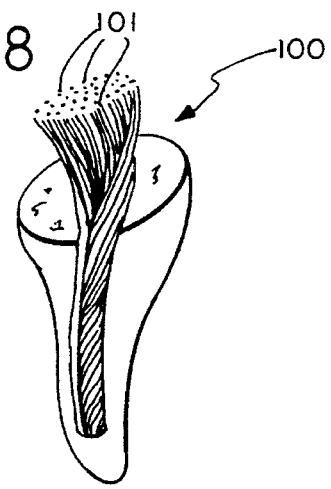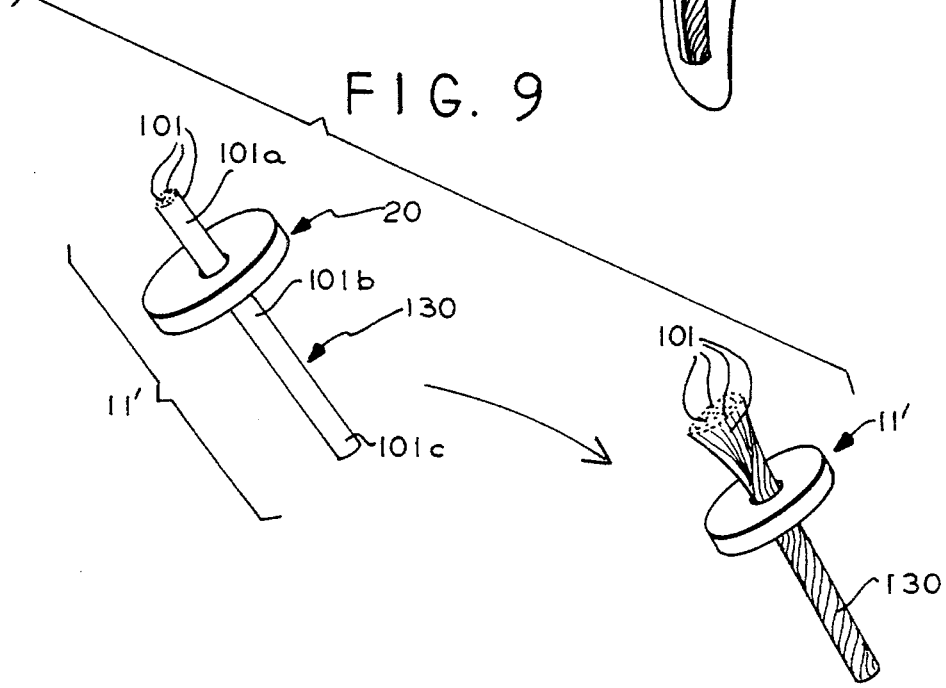

5,518,399

METHOD OF RESTORING AN ENDODONTICALLY-TREATED TOOTH

BACKGROUND OF THE INVENTION

The present invention generally relates to a dental post and core system for endodontically-treated teeth having a flexible, inelastic post. More specifically, this invention relates to an improved method of restoring endodontically-treated teeth.

Dental post and core systems are widely utilized to restore endodontically-treated teeth. Post and core restorations are routinely used to create an adequate foundation for the final restorative step, which may be a crown, onlay, or a fixed partial denture abutment. Generally, a post is provided for retention and lateral stability of the restoration. The core provides support for the crown. Two general types of post and core systems are known in the art: "active or screw-in" type systems and "passive" type systems. Active post and core systems mechanically engage the walls of the root canal and tooth dentin. Passive post and core systems are bonded in a reformed root canal utilizing cements and the like.

Two major problems are encountered when restoring an endodontically-treated tooth. Firstly, the tooth is more susceptible to fracture, and secondly, there is generally less coronal structure with which to work. The greater susceptibility of a tooth to fracture after endodontia may result from the tooth being more brittle. However, studies of the changing mechanical properties of pulpless teeth do not generally support this theory equating dryness with reduced mechanical strength. It appears that the greater susceptibility for fracture in an endodontically-treated tooth results from mechanical weakening of the tooth during root canal therapy and refinement of the canal. Improvements in restoration techniques that reduce mechanical weakening are therefore desirous.

An endodontically-treated tooth is generally severely compromised either due to trauma or neglect. Thus, traumatic fractures, removal of old restorations and carious tissue, and preparation of root canal access may not leave enough tooth to maintain the "dome effect" of the tooth or to retain a crown.

The stress concentrations in a tooth resulting from the prior art rigid post and core systems also play a vital role in tooth fracture. Stress concentrations can be impacted through system design and/or restoration techniques. Various studies and investigations into the susceptibility of endodontically-treated teeth to fracture and the contribution of prior art rigid dental post and core systems to such fracture have been conducted. *A Comparison of Intracanal Stresses in a Post-Restored Tooth Utilizing the Finite Element Method*, Cailleteau, Johnny G., Rieger, Monty R. and Akin, J. Ed, Journal of Endodontics, Vol. 18, No. 11, November 1992, pp. 540–544, reports that placement of a rigid post within a tooth alters the pattern of stress along the root canal as compared with an intact tooth. Instead of strengthening the tooth the post stiffens the coronal posted section and shifts the flexure point apically. The effect of this stiffening causes the nonposted apical portion of the tooth to deform at the post apex, resulting in a stress increase in that portion of the canal wall. Also, the cyclic loading and unloading of an incisor during mastication requires consideration of fatigue failure. Since the maximum bending stresses occur in connection with the apex of the post, any inclusions or defects within the wall of the dentin near the apical end of the post would create stress concentrations that increase the risk of a fatigue crack formation. Defects and microfractures introduced during endodontic treatment and post access preparation could become areas contributing to stress concentrations. Studies have also shown that more intact tooth structure provides better resistance to fracture than a metallic post. There is also evidence that stresses in the tooth tend to increase as the post diameter increases.

A flexible post eliminates these problems. A post and core system utilizing a flexible post shifts the stress concentrations coronally, eliminates the introduction of defects during post access preparation and post placement, and leaves more intact tooth.

The main function of a post is to provide retention to the core. Relieved of its expectation to facilitate resistence to tooth fracture, the post can be designed to optimize its retentive properties. Several factors govern the retentiveness of endodontic posts. The shape of the post and its length are among the essential factors. Tapered dowels have been found to be significantly less retentive than parallel-sided posts. A serrated 5.5 mm parallel-sided dowel was found more retentive than an 8 mm tapered post. Tapered posts provide high shoulder stresses but an undesirable wedging effect. The wedging effect results in part from the prior art placement of a rigid post in a naturally curved and varying diameter root canal. Active posts are very retentive, but may impose too much stress on the tooth, especially compromised teeth. Thus it appears that a passive, serrated, parallel-sided post is a preferred structure for dental post and core systems. A flexible, passive, serrated parallel-side post provides the previously-mentioned advantages in preventing tooth fracture and additionally permits the post to extend for a greater length into the root canal for improved retention.

In addition to post shape and length adequate retention is a function of cementing mechanisms. Various cementing medium have been studied. Utilization of low viscosity resin cement in combination with smear layer removal can be considered a universal post cementation technique. In addition to good retention, this cementing technique offers the benefits of a cement with very little resistance to post insertion, thereby minimizing stresses applied to tooth structure during cementation. Generally, however, the invention of the present disclosure is not limited by the cementing process used.

An elastic, wire pin having a plurality of flexible, radially-extending fins along its length is disclosed in German Patent No. DE 3643-219 to Weisskircher. While providing some advantages over the prior art rigid post, the "high degree of elasticity" of the Weisskircher pin will cause it to try and retain its initial shape in the canal. During and after placement, flexing of the pin will cause the apical end of the pin to lay against the wall of the root canal. Stress concentrations in the tooth as known for rigid posts will thereby be induced. A pin formed from wire also has low retention characteristics and tends to rotate within the root canal. Radial fins are utilized in the Weisskircher disclosure to resist rotation of the wire pin. However, these radial fins may become further sources of stress concentrations and fatigue failure as the wire pin rotates. No prior art known to the present Applicants discloses or suggests a post in a dental post and core system that is flexible and inelastic, i.e. that conforms to the shape of the root canal to eliminate the stress concentrations that facilitate tooth fracture.

U.S. Pat. No. 4,778,389 to Salvo discloses a dental post construction to eliminate lateral stress in a tooth wherein a rigid, split post is formed by parallel sections joined at a marginal top portion of the post head.

U.S. Pat. No. 5,073,112 to Weil discloses a dental post having an active portion and a passive portion.

U.S. Pat. No. 5,074,792 to Bernadat discloses a passive post and core system comprising a rigid peg disposed in a porous sheath formed of high-strength filaments.

International Search Publication No. WO 91/07142 (PCT/FR90/00831) to Reynaud et al. discloses a dental post and core system having a post formed from equally-tensioned fibers of composite material.

U.S. Pat. No. 4,936,776 to Kwiatkowski discloses a translucent post and core structure to minimize gingival discoloration adjacent a dental restoration.

U.S. Pat. No. 3,949,476 to Kahn discloses a "direct" method of restoring an abraded or broken tooth.

Swiss Patent No. 1,457,914 to Stomatology Research Institute discloses a method of making a pin stump insert.

West German Patent No. 1,541,209 to Kurer discloses the now-conventional threaded, screw-in type active post.

Currently-marketed dental post and core systems such as the FLEXI-POST, the DENTATUS POST, the RADIX POST and the BRASSELEAR screw posts all advocate screwing threaded rigid posts into straight paths machined into the tooth dentin. The present day posts are also generally formed from rigid metals such as steel, titanium and other alloys which do not flex in the same manner as a natural tooth. This differential in flexibility between the natural tooth and the post may cause tooth fracture when the restored tooth is stressed during mastication or from trauma. Cast post are subject to these same limitations and require an additional laboratory fee and an additional visit to the dentist to complete the procedure.

A means to quickly and easily identify the components of a post and core system is also needed in the prior art. Presently, there is either no color coding of post and core systems or the color identification consists of an inconspicuos dot of color. Bright color identification of post and core systems would significantly advance the art. The lack of a color protocol in the prior art creates confusion, eye strain and a sloppy work environment. The inability to readily identify each post and core by sight creates problems before, during and after the procedure is completed. Firstly, before the procedure is initiated the dentist and staff must select the post and core and isolate it from others that may be very close in size. During the procedure the dentist must carefully avoid confusing the selected post and core. After the procedure the used and unused devices must be readily identified for contamination control. Further, a post and core system installed by one dentist may later require an emergency or other procedure by a different dentist in a completely different part of the world. Color-coded identification would eliminate uncertainty and guesswork.

The post and core system of the present invention overcomes all of these limitations of the prior art.

SUMMARY OF THE INVENTION

The present invention is a method of restoring endodontically-treated teeth utilizing a dental post and core system that includes a flexible, inelastic post. The flexible post conforms to the curvature of the root canal during placement and reduces mechanical weakening of an endodontically-treated tooth by eliminating stress concentrations at the apical end of the post, by reducing the size of canal access preparations and by allowing more intact tooth to be retained.

The present invention also provides a method of restoring an endodontically-treated tooth that reduces the time and equipment needed during a procedure and lessens the chance that a dentist will perforate or fracture the canal wall during placement of a post.

An object of the present invention is to provide a method for restoring endodontically-treated teeth that reduces the susceptibility for tooth fracture.

Another object of the present invention is to provide a method of restoring endodontically-treated teeth that reduces the mechanical weakening of tooth structure by relieving stress concentrations.

Another object of this invention is to provide a method of restoring endodontically-treated teeth that eliminates drilling for post placement and that can be installed using inexpensive, readily available endodontic drills.

A still further object of this invention is to provide a method of restoration for teeth previously classified as hopeless and difficult, such as hemisected and dilacereted teeth and other conditions of extreme loss of tooth structure.

These and other objects and advantageous of the improved dental post and core system of the present invention will be apparent to those skilled in the art from the following description of preferred embodiments, claims and appended drawings.

BRIEF DESCRIPTION OF THE DRAWINGS

FIG. 1 is a lateral cross-sectional view of the first preferred embodiment of the dental post and core system of the present invention.

FIG. 2 is a lateral cross-sectional view of a first preferred embodiment of the present invention in a double-canal tooth.

FIG. 3 is a perspective, exploded view of a first core spacer and a first post reinforcing rod of the present invention.

FIG. 4 is a lateral cross-sectional view of a second post reinforcing rod constructed in accordance with the teachings of the present invention.

FIG. 5 is a partially cross-sectioned perspective view of a third post reinforcing rod constructed in accordance with the teachings of the present invention.

FIG. 6 is a top perspective view of a second built-up core spacer in accordance with the teachings of the present invention.

FIG. 7 is a lateral cross-sectional view taken along line 7—7 of FIG. 6.

FIG. 8 is a perspective view of a second preferred embodiment of the dental post and core system of the present invention.

FIG. 9 is a perspective view of a third preferred embodiment of the dental post and core system of the present invention.

DESCRIPTION OF THE PREFERRED EMBODIMENTS

FIG. 1 illustrates in a lateral cross-sectional view a first preferred embodiment of the dental post and core system 1 of the present invention. First system 1 generally comprises a core 10 and flexible post 11. Post 11 includes a core spacer 20 and a flexible, inelastic post reinforcing rod 30 extending apically from the core spacer 20. The post reinforcing rod 30 may be cylindrical or tapered. Further, core spacer 20 may be flexible and/or resilient. In the first dental post and core system 1, core spacer 20 and reinforcing rod 30 are shown to be seperately constructed. A bore 21 in core spacer 20 selectively engages an upper portion 31 of post reinforcing rod 30. However, core spacer 20 and reinforcing rod 30 may be integrally formed without departing from the spirit and scope of the present invention. The separable construction of core spacer 20 and the reinforcing rod 30 permits fabrication of built-up post and core systems 1 in a variety of configurations from readily identifiable components. Core 10 is seated on the core spacer 20 and a crown 2, for example, is placed over the core 10 as known in the art.

The teachings of the present invention may be utilized for restoration of multi-rooted teeth having two, three or four diverging canals. In the second dental post and core system 1' for a double-rooted tooth illustrated in FIG. 2 it can be seen that said second system 1' includes a second core spacer 20' having two bores 21a, 21b which engage respective flexible post reinforcing rods 30.

The advantages of a flexible post 11 in a dental post and core system are numerous. Firstly, a flexible post 11 can follow the contours of the root canal 3. This method of placement eliminates or reduces the amount of drilling required for root canal therapy and for preparation of the canal access. The reinforcing rods 30 can be appropriately sized to permit use of commonly-used dental drills. More intact tooth is left in place which has been shown to provide the best resistance to tooth fracture. The flexible, inelastic post reinforcing rod 30 of the present invention also eliminates stress concentrations in the canal wall and dentin due to the apical lateral movement of rigid and elastic posts. Utilizing a flexible post 11 the intracanal stress at the apical level is shifted coronally to the area of maximum stress. The core spacer 20 absorbs the intracanal stresses by deformation of the body of the core spacer 20. Core spacer 20 therefore can be seen to serve as both a seat for the core 10 and as a stress absorber. A flexible post 11 also reaches further apically which provides greater retention. This is specifically applicable to the restoration of teeth that have suffered extreme loss of tooth structure where to gain adequate retention the length of the post must enter the curved portion of the root canal 3.

In the first preferred embodiment of the flexible post 11 in the first dental post and core system 1 of the present invention, illustrated in an exploded, perspective view in FIG. 3, the core spacer 20 and the flexible post reinforcing rod 30 are formed from identical material. This, however, should not be understood to be a limitation of the present invention. The core spacer 20 may be formed of a first material to optimize its stress-resistance characteristics; reinforcing rod 30 may be formed of a second material to optimize its retention characteristics. Core spacer 20 and post reinforcing rod 30 are preferably formed from reinforced plastics such as fiberglass polyester composites similar to those used in the construction of fishing poles, flexible ceramic resin composites, graphites, teflons, polycarbonates and the like. Metals, such as pure or alloyed titanium, steel, platinum, palladium and the like, can be processed into fibers and bound in a matrix of resin or other binders for fabrication of the core spacer 20 and post reinforcing rod 30. The flexibility of these materials is close to the flexibility of the natural tooth and therefore will reduce the flexibility differential of the intact tooth and the inserted post 11. Fiberglass polyester composites and the like are also well suited for in-office etching of the surfaces of the core spacer 20 and reinforcing rod 30 for better and stronger cementation. Reinforcing rod 30 may also be treated with dental adhesives and bonding agents such as silane urethane, bisgma and acrylic resins to increase retention. Core spacer 20 and post reinforcing rod 30 also preferably include an appropriate amount of radiopaque material such as titanium oxide, barium sulfate and other materials known in the dental industry to insure X-ray documentation.

The first preferred embodiment of the flexible post 11 is preferably color coded for identification purposes. In the first preferred flexible post 11, the core spacer 20 and reinforcing rod 30 are color identified according to the inside diameter of the bore 21 in core spacer 20, identified in FIG. 3 by the letter "B", and the outside diameter of the reinforcing rod 30, identified in FIG. 3 by the letter "D". In the preferred embodiment the reinforcing rods 30 are formed having the following diameters "D": 0.036 inch, 0.040 inch, 0.050 inch, 0.060 inch, and 0.070 inch. The bores 21 of the respective core spacers 20 have a corresponding bore diameter "B" (marginally larger than rod diameter "D") for snug engagement of the spacer 20 to an upper portion 31 of the post reinforcing rod 30. Bright colors are preferably used. The following color protocol is preferred:

| "B", "D" | Color |
| --- | --- |
| .036 inch | White |
| .040 inch | Yellow |
| .050 inch | Red |
| .060 inch | Blue |
| .070 inch | Green |

A second dental post and core system 2 for multi-rooted teeth, as illustrated in FIG. 2, may have a second core spacer 20' wherein the respective first and second bores 21a, 21b are sized differently for placement of reinforcing rods 30 of different size. Prefabricated multiple root dental post and core systems 2 having differently sized reinforcing rods 30 will be multicolored in accordance with the above protocol. For example, a second core spacer 20' may have a yellow ring around first bore 21a and a white ring around second bore 21b to indicate that this core spacer 20' is to be utilized with a 0.040 inch reinforcing rod 30 in first bore 21a and a 0.036 inch reinforcing rod 30 in second bore 21b.

FIG. 4 illustrates in a front plan view a second preferred embodiment of a reinforcing rod 40 constructed in accordance with the teachings of the present invention. Second reinforcing rod 40 is a tapered, flexible elongated member 41. The outer wall of the elongated member 41 includes a plurality of displaced circumferential serrations 42 and a channel 43 extending longitudinally between the respective serrations 42. The combination of flexibility in the second reinforcing rod 40 and the displacement of the respective serrations 42 is believed to reduce the wedging effect of rigid posts as known in the art.

A third preferred embodiment of a reinforcing rod 50 is illustrated in FIG. 5. Third reinforcing rod 50 comprises a closed flexible sheath 51 having a compressible gel 52 disposed within the interior of the sheath 51. During placement of the third reinforcing rod 50 the wall 51a of the sheath 51 deforms to the varying diameter and curvature of the root canal.

From the foregoing, it should be readily understood that the respective first, second and third reinforcing rods 30, 40 and 50 may be utilized in conjunction with a core spacer 20 or a prefabricated or built-up core 10 may be attached directly to the coronal end of the reinforcing rod 30, 40, 50. A prefabricated core 10 for attachment directly to a reinforcing rod 20, 40, 50 may include a bore 21 extending therethrough as illustrated for the core spacer 20 of the present invention. Reinforcing rods 30, 40 and 50 may be pre-cut or formed in an extended length to provide a margin of safety for mistakes in measuring.

The core spacer 20 of the present invention may be prefabricated in standard sizes or built-up in the dentist's office. The external shape of core spacer 20 generally corresponds to the concavity of the chamber formed in root canal therapy. In teeth with a shallow concavity standard dental drills may be used to machine a contersunk region in the tooth for receipt of core spacer 20. FIG. 6 illustrates in a top perspective view a preferred embodiment of a built-up core spacer 20' constructed in accordance with the teachings of the present invention. The flexible reinforcing rod 30 is placed into the root canal 3 (FIG. 7). Built-up core spacer 20' is then formed about the coronal end of first reinforcing rod 30 by injection of any of the suitable fast-setting liquids or pastes known in the art. Built-up core spacer 20' initially extends to the top of the tooth dentin 4 and into any fractures 4a or the like in the tooth. A recessed ring 25 is then reamed into the top of the built-up core spacer 20' along the inside edge of the tooth to form a central, raised portion 26 of the built-up core spacer 20'. It is preferred that the floor 25a of the recessed ring 25 is approximately 1.5 mm below the top of the tooth dentin 4. As can be seen in the cross-sectional view of the built-up core spacer 20' illustrated in FIG. 7 a core 10 is seated onto the top of the central, raised portion 26 and the floor 25a of the recessed ring 25. Preferably, sufficient lateral space is left so that the crown 2 may be fitted over the core 10 to likewise rest on the floor 25a of the recessed ring 25 approximately 1.5 mm below the top of the tooth.

A mutable flexible post 100 is illustrated in FIG. 8 and a mutable post reinforcing rod 130 is illustrated in FIG. 9. Mutable post 100 and mutable post reinforcing rod 130 are preferably formed from a bundle of reinforced plastic or other fibers 101 cemented together at the central portion 101b and the lower portion 101c of the fibers 101. The upper portion 101a of the fibers 101 is loosely compacted so that the upper portion 101a may be selectively flared to provide additional surface area to scaffold a built-up core. Flaring of the upper portion 101a of the fibers 101 may be performed at the factory or in the dentist's office using standard crimping pliers. A prefabricated core (not shown) may be attached to the coronal aspect of the mutable post 100 when it is disposed in its unflared position.

As shown in FIG. 9 the mutable reinforcing rod 130 constructed in accordance with the teachings of the present invention may likewise be utilized in a flared or unflared position. A first core spacer 20 is attached to the coronal end of the mutable reinforcing rod 130. The mutable post 11' comprising a first core spacer 20 and a mutable reinforcing rod 130 may be used to support a prefabricated core, or the coronal end of the mutable post 11 may be flared to form a scaffold for a built-up core. An advantage of this preferred embodiment of the present invention is that a single construction can be used for either a prefabricated core, or by simply crimping the coronal end of the mutable post reinforcing rod 130 it may be used to support a built-up core.

Various changes, additions and modifications of the present invention may be made to the preferred embodiments without departing from the spirit and scope of the present disclosure. Such changes, additions and modifications within a fair reading of the following claims are intended to be part of the present invention.

Therefore, in view of the foregoing, we claim:

1. A method of restoring an endodontically-treated tooth to reduce the susceptibility for tooth fracture, said method comprising the steps of:

placing a flexible mutable reinforcing rod into a root canal, said flexible mutable reinforcing rod having a coronal end and an apical end, flaring said coronal end of said mutable reinforcing rod, and attaching a dental core to said flared end of said mutable reinforcing rod.

2. A method of restoring an endodontically-treated tooth to reduce the susceptibility for tooth fracture as in claim 1, said method further comprising the steps of:

attaching a core spacer to said coronal end of said flexible mutable reinforcing rod, and attaching said dental core to an upper portion of the core spacer.

3. The method as in claim 1, wherein said reinforcing rod comprises a compressible gel within a deformable sheath.

4. The method as in claim 1, wherein said flexible reinforcing rod comprises a bundle of flexible fibers.

5. A method of restoring an endodontically-treated tooth to reduce the susceptibility for tooth fracture, said method comprising the steps of:

placing a flexible, mutable post comprising a flexible reinforcing rod into a root canal, said reinforcing rod having a coronal end and an apical end, extending said coronal end of said flexible mutable reinforcing rod through a core spacer, flaring said coronal end of said flexible mutable reinforcing rod, and attaching a dental core to said flared end of said mutable, flexible reinforcing rod.

6. A method of restoring an endodontically-treated tooth to reduce the susceptibility for tooth fracture as in claim 5, said method further comprising the step of:

attaching said dental core to an upper portion of said core spacer.

7. A method of restoring an endodontically-treated tooth to reduce the susceptibility for tooth fracture, said method comprising the steps of:

placing a flexible reinforcing rod into a root canal of a tooth, said flexible reinforcing rod having a coronal end and an apical end, forming a built-up core spacer at said coronal end of said flexible reinforcing rod, cutting a recessed ring into a top portion of said core spacer below the top of the tooth, and forming a built-up core onto said top portion of said core spacer and within said recessed ring.

* * * * *